United States Patent [19]

Green

[11] Patent Number: 5,358,714
[45] Date of Patent: Oct. 25, 1994

[54] COSMETIC COMPOSITION

[75] Inventor: Martin R. Green, Buckingham, United Kingdom

[73] Assignee: Unilever Patent Holdings B.V., Rotterdam, Netherlands

[21] Appl. No.: 995,312

[22] Filed: Dec. 22, 1992

Related U.S. Application Data

[63] Continuation of Ser. No. 807,780, Dec. 10, 1991, abandoned, which is a continuation of Ser. No. 538,601, Jun. 14, 1990, abandoned, which is a continuation of Ser. No. 326,952, Mar. 22, 1989, abandoned.

[30] Foreign Application Priority Data

Mar. 23, 1988 [GB] United Kingdom ............... 8806891

[51] Int. Cl.$^5$ .................. A61K 9/00; A61K 7/06; A61K 37/02
[52] U.S. Cl. ..................... 424/400; 424/70; 424/401; 514/547
[58] Field of Search ............ 424/70, 400, 401; 514/546, 552, 599, 786, 275

[56] References Cited

U.S. PATENT DOCUMENTS

| | | | |
|---|---|---|---|
| 4,139,619 | 2/1979 | Chidsey, III | 424/45 |
| 4,745,103 | 5/1988 | Oono et al. | 424/70 |
| 4,832,946 | 5/1989 | Green | 424/115 |

FOREIGN PATENT DOCUMENTS

| | | |
|---|---|---|
| 102534 | 8/1983 | European Pat. Off. |
| 0102534 | 3/1984 | European Pat. Off. |
| 129778 | 6/1984 | European Pat. Off. |
| 0334585 | 9/1989 | European Pat. Off. |
| 3522853 | 6/1986 | Fed. Rep. of Germany |
| 61-15809 | 6/1986 | Japan |
| 61-15816 | 6/1986 | Japan |
| 62-230710 | 10/1987 | Japan |
| 61-32808 | 11/1987 | Japan |
| 8504577 | 10/1985 | World Int. Prop. O. ..... A61K 7/00 |

OTHER PUBLICATIONS

Ogawa, H. and Hattori, M., "Regulation Mechanism of Hair Growth", appeared in "Normal and Abnormal Epidermal Differentiation", edited by Seiji, M. and Bernstein, I. A., at pp. 159–170 and published by the University of Tokyo Press, Tokyo in 1983.

Hideo Uno, "Pharmacological Aspects of Hair Follicle Growth" at p. 41 of the Proceedings of the Symposium organized by the Societe de Recherche Dermatologique on "The Human Hair Follicle in Biomedical Research" held in Brussels on 5–6 Feb. 1988.

Inohara, S. et al. in "Skin Res." 29(2) 157–168 (1971).
[Translation] "Role of Information Tranmission Mechanisms in Differentiation and Proliferation of Epidermal Cells—with Special Reference to C Kinase" Inohara, et al. Hifu (Skin) vol. 29, No. 2 1987 pp. 157–168.

Primary Examiner—Thurman K. Page
Assistant Examiner—William E. Benston, Jr.
Attorney, Agent, or Firm—Milton L. Honig

[57] ABSTRACT

A preserved composition suitable for topical application to mammalian skin or hair for inducing, maintaining or increasing hair growth comprises:

(i) a chemical activator of protein kinase C enzymes chosen from diacylglycerols having the structure (1):

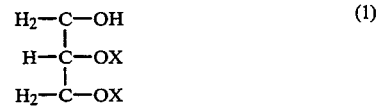

where X is the same or different, and is represented by the grouping:

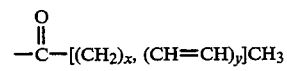

where x is 0, or an integer of from 1 to 28, and y is 0 or an integer of from 1 to 5;

the R groups being of either stereochemical configuration with respect to the carbon backbone of the glycerol molecule, and the double bonds beings of either cis or trans configuration; and (ii) a cosmetically acceptable vehicle for the chemical activator.

8 Claims, No Drawings

COSMETIC COMPOSITION

This is a continuation application of Ser. No. 07/807,780 filed Dec. 10, 1991, now abandoned, which was a continuation of Ser. No. 07/538,601 filed Jun. 14, 1990, now abandoned, which was a continuation of Ser. No. 07/326,952 filed Mar. 22, 1989, now abandoned.

FIELD OF THE INVENTION

The invention relates to cosmetic and pharmaceutical compositions for topical application to mammalian skin or hair, containing certain diacylglycerols as enzyme activators which are capable of promoting hair growth, especially terminal hair growth on the human scalp.

BACKGROUND

The Hair Growth Cycle

It should be explained that in most mammals, hair does not grow continuously, but undergoes a cycle of activity involving alternate periods of growth and rest. The hair growth cycle can be divided into three main stages, namely:

(i) the growth phase known as anagen, during which the hair follicle penetrates deep into the dermis with the cells of the bulb dividing rapidly and differentiating to form the hair, (ii) the transitional stage known as catagen, which is heralded by the cessation of mitosis, and during which the follicle regresses upwards through the dermis and hair growth ceases, (iii) the resting stage known as telogen, in which the regressed follicle contains a small secondary germ with an underlying ball of tightly packed dermal papilla cells.

The initiation of a new anagen phase is revealed by rapid proliferation in the germ, expansion of the dermal papilla and elaboration of basement membrane components. The hair cycle is then repeated many times until, as a consequence of the onset of male pattern baldness, most of the hair follicles spend an increasing proportion of their time in the telogen stage, and the hairs produced become finer, shorter, and less visible; this is known as terminal to vellus transformation.

PRIOR ART

Alleged Baldness Cures

Although there have been many claims in the scientific literature to the promotion or maintenance of hair growth by the topical application of hair tonics and the like, with the possible exception of minoxidil, none has been shown to be sufficiently free from disadvantageous clinical side effects, whether administered topically, orally or systemically, to warrant commercial exploitation as an ethical pharmaceutical, proprietary medicine, or as a cosmetic product. Possibly, the only means which has met with partial success for growing hair on the bald or balding human head is by transplantation of hair to the bald areas. This is, however, an extremely painful operation and is not always successful. Furthermore, it is immediately apparent to the casual observer that the subject has received a hair transplant and it may take many months or even years before hair regrowth, following this operation, assumes an appearance which resembles that of the original naturally growing hair.

Among the many hair regrowth studies that have been reported in the literature, there is included the work of Bazzano as described in PCT International Publication No. WO 85/04577. This publication describes a composition which is useful for increasing the rates of hair growth on mammalian skin, prolonging the anagen phase of the hair growth cycle and for treating various types of alopecias. The composition in question comprises a pyrimidine carbamate.

It has also been reported in U.S. Pat. No. 4,139,619 to Chidsey assigned to the Upjohn Company, that a topical composition comprising minoxidil as the free base or acid addition salt thereof, or certain specified related iminopyrimidines, is useful in stimulating the conversion of vellus hair to growth as terminal hair, as well as increasing the rate of growth of terminal hair.

In spite of the apparent stimulation of hair growth or regrowth reported independently by Bazzano and Chidsey, following topical application of minoxidil or related compounds, there is general concern that systemic side-effects can result, particularly following topical application of minoxidil. Thus it is generally recognised in the medical literature that the side effects of orally administered minoxidil are very serious, and include fluid retention, tachycardia, dyspnea, gynecomastia, fatigue, nausea and cardiotoxicity.

Background to the invention

In addition to the alleged benefits of employing the pyrimidine carbamates of Bazzano or minoxidil of Upjohn, Ogawa H., and Hattori, M. in a paper entitled "Regulation Mechanism of Hair Growth" which appeared in "Normal and Abnormal Epidermal Differentiation" edited by Seiji, M. and Bernstein, I. A., at pages 159–170 and published by the University of Tokyo Press, Tokyo in 1983, first reported that topical phorbol ester could enhance hair growth of mice. It was, however, not until five years later that these results were repeated by Hideo Uno, and in a paper entitled "Pharmacological Aspects of Hair Follicle Growth" at page 41 of the Proceedings of the Symposium organised by the Societe de Recherche Dermatologique on "The Human Hair Follicle in Biomedical Research" held in Brussels on Feb. 5–6, 1988, he reported that topical application of phorbol ester to rat skin has a "minoxidil-like" effect and stimulates hair growth. Phorbol esters are known to act by binding to and activating protein kinase C, a molecule which has been implicated in the control of cell proliferation and which resides (in its activated form) in the plasma membrane. Uno suggests that assay of the activity of protein kinase C may be a marker "for the effect of drugs on follicular growth". Phorbol esters are known to be potent tumor promoters, and consequently have no commercial value as hair growth products.

There are, however, other molecules described in the literature which can activate protein kinase C. Inohara, S., et al in Skin Res. 29(2) 157–168 (1987), for example, report that OAG (a diacylglycerol) stimulates thickening of epidermal cells and increased hair follicle hyperplasia to the same degree as TPA (a phorbol ester). This diacylglycerol is known to interact with protein kinase C.

We have now discovered that topical application of certain diacylglycerols can stimulate hair growth via the activation of protein kinase C, firstly using the rat model employing methodology to be described later in this specification, and subsequently using human subjects showing male pattern baldness.

DEFINITION OF THE INVENTION

Accordingly, the invention provides a preserved composition suitable for topical application to mammalian skin or hair for inducing, maintaining or increasing hair growth which comprises:

(i) a chemical activator of protein kinase C enzymes chosen from diacylglycerols having the structure (1):

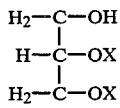

where X' is the same or different, and is represented by the grouping:

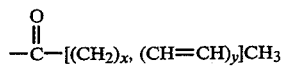

where x is 0, or an integer of from 1 to 28, and y is 0, or an integer of from 1 to 5;
the OX groups being of either stereochemical configuration with respect to the carbon backbone of the glycerol molecule, and the double bonds being of either cis or trans configuration; and (ii) a cosmetically acceptable vehicle for the chemical activator;

the total amount of chemical activator present in the composition being sufficient to increase hair growth in the rat, when said composition is applied topically thereto over a period of no more than 3 months, by at least 10% more than that obtainable using a control composition from which the said activator has been omitted, in accordance with the Rat Hair Growth Test.

DISCLOSURE OF THE INVENTION

THE CHEMICAL ACTIVATOR OF PROTEIN KINASE C ENZYMES

By "chemical activator" is meant a substance which is not only physiologically suitable and safe for topical application to skin, but which is capable of activating protein kinase C enzymes.

By "preserved composition", is meant that the composition is free from microbial contaminants capable of resulting in microbial spoilage of the composition and/or biodegradation of the chemical activator.

The chemical activator is chosen from diacylaglycerols having the structure (1):

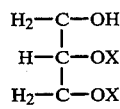

where X is the same or different and is represented by the grouping:

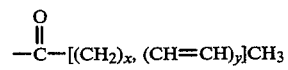

where x' is 0, or an integer of from 1 to 28, and y is 0, or an integer of from 1 to 5;
the OX groups being of either stereochemical configuration with respect to the carbon backbone of the glycerol molecule, and the double bonds being of either cis or trans configuration.

Particularly preferred examples of diacylglycerols derived from the above generic structure (1) include the following:

1,2-Dibutanoyl-rac-glycerol
1,2-Dihexanoyl-sn-glycerol
1,2-Dioctanoyl-rac-glycerol
1,2-Dioctanoyl-sn-glycerol
1,2-Didecanoyl-rac-glycerol
1-Oleoyl-2-acetyl-rac-glycerol
1-Oleoyl-2-acetyl-sn-glycerol
1-Stearoyl-2-arachidonoyl-sn-glycerol
1,2-Distearoyl-rac-glycerol
1,2-Dipentadecanoyl-sn-glycerol
1,2-Dipentadecanoyl-rac-glycerol
1,2-Dipalmitoyl-rac-glycerol
1,2-Dipalmitoyl-sn-glycerol
1,2-Diseptadecanoyl-rac-glycerol
1,2-Dioleoyl-sn-glycerol
1,2-Dioleoyl-rac-glycerol
1,2-Diarachidonoyl-sn-glycerol
1,2-Dieicosanoyl-sn-glycerol
1,2-Didoeicosanoyl-rac--glycerol, and
1,2-Dioctaeicosanoyl-sn-glycerol.

Mixtures comprising two or more of the chemical activators can be employed in the composition according to the invention.

The total amount of chemical activator present in the composition according to the invention is sufficient to increase hair growth in the rat, the model selected for this test, when said composition is applied topically thereto over a period of no more than 3 months, by at least 10% more than that obtainable using a control composition from which the said activator has been omitted, this assessment being carried out in accordance with the Rat Hair Growth Test.

Preferably, the amount of chemical activator should be sufficient to increase hair growth in the rat by at least 15%, more preferably by at least 20%, most preferably by at least 30% and ideally by more than 30%.

The sufficient amount will depend on the effectiveness of a chemical activator some being more effective than others, but in general, an amount of from 0.000001 to 99.9%, preferably from 1 to 50% by weight of the composition will provide an adequate dose to the skin after topical application.

Preservation of the Composition

The composition according to the invention is preferably preserved in such a manner that it will enjoy an extended shelf life following manufacture and prior to sale and use. Ideally the composition will have an indefinite shelf life.

It is accordingly apparent that the chemical activator is likely to be prone to attack by bacteria, moulds and fungi and other microbial influences, particularly at pH values near neutrality that characterise the preferred composition. The shelf-life of the composition can therefore be unacceptably short due to the biodegradation of the activator unless steps are taken to preserve the composition.

In order to be preserved, the composition should preferably be free, or substantially free, from viable microbial contaminants that are capable of resulting in microbial spoilage of the composition, and/or biodegradation of the activator prior to topical application of the composition to mammalian skin or hair. It is to be understood, however, that the invention is also concerned with compositions, as herein defined, which may contain viable but dormant microorganisms, such as bacterial spores, provided that the conditions of preservation do not result in substantial proliferation of the microorganisms prior to use of the composition.

Examples of methods that can be employed to achieve preservation of the composition, includes the following:

(i) Sterilisation

The composition according to the invention can be preserved by sterilisation to remove or kill substantially all viable microbial contaminants. This can be achieved for example by irradiation using a lethal dose of gamma rays, by heat sterilisation or by ultrafiltration using techniques that are well established in the pharmaceutical industry.

(ii) Extremes of pH value

The composition according to the invention can alternatively be preserved by adjusting its pH to a value that is either too low (e.g. pH <2) or too high (e.g. pH >12) to permit significant proliferation of microbial contaminants. The pH of the composition can accordingly be adjusted to desired high or low values by addition of an alkali or acid as a pH adjustant.

(iii) Chemical Preservative

The composition according to the invention can also be preserved by including in it a chemical preservative which functions to prevent the growth of or kill bacteria, fungi or other microorganisms.

Examples of chemical preservatives include ethanol, benzoic acid, sodium benzoate, sorbic acid, potassium sorbate, sodium propionate and the methyl, ethyl, propyl and butyl esters of p-hydroxybenzoic acid. The amount of chemical preservative that can be incorporated in the composition according to the invention will generally be from 0.05 to 5%, preferably from 0.1 to 2% by weight, the amount chosen being sufficient to arrest microbial proliferation.

(iv) Water activity depressants

The composition according to the invention can also be preserved by the inclusion of a water activity depressant such as glycerol, propylene glycol, sorbitol, sugars and salts, for examples alkali metal halides, sulphates and carboxylates. When employing a water activity depressant, sufficient should be incorporated in the composition according to the invention to reduce the water activity ($\delta_w$) from 1 to <0.9, preferably to <0.85 and most preferably <0.8, the lowest of these values being that at which yeasts, moulds and fungi will not proliferate.

The Vehicle

The composition according to the invention also comprises a solid, semi-solid or liquid cosmetically and/or physiologically acceptable vehicle, to enable the chemical activator to be conveyed to the skin or hair at an appropriate dilution. The nature of the vehicle will depend upon the method chosen for administration of the composition to the skin. The vehicle can itself be inert or it can possess physiological or pharmaceutical benefits of its own.

It should be explained that vehicles are substances which can act as diluents, dispersants, or solvents for the chemical activator, which therefore ensure that it can be applied to and distributed evenly over the hair and/or skin, especially the scalp, at an appropriate concentration. The vehicle is preferably one which can aid penetration of the chemical activator into the skin, particularly to reach the immediate environment of the hair follicle, thereby improving its ability to enhance the activity of protein kinase C. The role and identity of selected vehicles as activity enhancers is described later in this specification.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, ispropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, dimethylpolysiloxane, di-n-butyl sebacate, isopropyl myristate, isopropyl palmitate, isopropyl stearate, butyl stearate, polythylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminium silicate, fumed silica, carboxyvinyl polymer, sodium carboxymethyl cellulose, ethylene glycol monostearate.

Activity Enhancer

The vehicle present in the composition according to the invention preferably functions as or comprises an activity enhancer to aid penetration of the activator into and/or through the skin, or otherwise to enhance its benefits in increasing hair growth.

The activity enhancer can be chosen from a wide variety of molecules, in addition to some of the vehicles as hereinbefore described, which can function in different ways to enhance the benefits of the partial degredation products. Particular classes of activity enhancers include other hair growth stimulants, penetration enhancers and cationic polymers, whose presence can further improve the delivery of the chemical activator through the stratum corneum to its site of action.

Some activity enhancers can also function as vehicles for the chemical activator.

The means for enhancing the activity of the chemical activators can also take the form of an iontophoretic device as will be explained later. This and other means for enhancing the activity of said chemical activators are now disclosed in greater detail.

(a) Other Hair Growth Stimulants

Examples of other substances which themselves possess the ability to stimulate or increase hair growth include, for example;
Benzalkonium chloride
Benzethonium chloride
Phenol
Estradiol
Diphenhydramine hydrochloride
Chlorpheniramine maleate
Chlorophyllin derivatives
Cholesterol
Salicylic acid
Cystine
Red pepper tincture
Benzyl nicotinate
dl-Menthol
Peppermint oil
Calcium pantothenate
Panthenol
Castor oil
Hinokitiol
Prednisolone
Resorcinol
Retinoids, or pharmaceutically acceptable esters, ethers or salts thereof.

Further substances which themselves possess the ability to increase the rate of terminal hair growth include:
(i) δ-1,4 esterified disaccharides described by Choay S.A. in EP-A-O 064 012, having the structure (50):

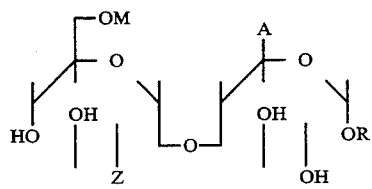

(50)

where
Z represents a functional nitrogen group, such as an azide or a group having the structure —NHB, in which B represents —H or a functional group such as acetyl or sulphate as a salt with an organic or mineral cation;
M represents —H or $SO_3M_1$, where $M_1$ is an organic or metallic cation, particularly an alkali metal; or an acetyl group;
R represents a $C_1$ to $C_4$ alkyl radical, especially methyl; or an aryl radical;
A represents a functional group such as an acid or —$COOR_1$, where $R_1$ represents —H or a $C_1$ to $C_4$ alkyl radical, especially methyl; or a metal, especially an alkali metal;

(ii) esterified oligosaccharides as described by Unilever in EP-A-O 211 610, including at least one esterified disaccharide unit consisting of a uronic acid residue having the structure (51):

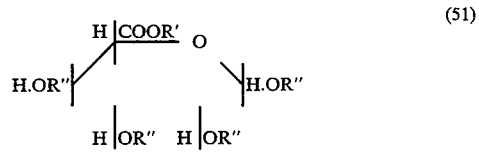

(51)

and a hexosamine residue having the structure (52):

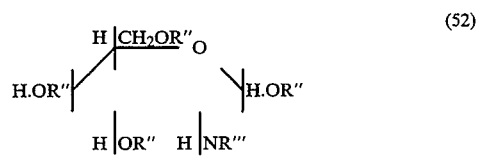

(52)

where
R' is —H, $C_3$ to $C_{10}$ alkyl or

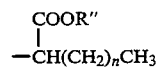

R" is —H, $C_1$ to $C_4$ alkyl, —$CO(CH_2)_mCH_3$, —$SO_3M'$,
R''' is —H, —$CO(CH_2)_mCH_3$, or —$SO_3M'$,
M' is —H, or a metallic or organic cation
n is 0 or an integer of from 1 to 7, and
m is 0 or the integer 1 or 2;
the groups designated R" being the same or different, one R" group from each pyranose ring structure being linked by a glycosidic linkage having the configuration δ-1,3, δ-1,4, β-1,3 or β-1,4; and the —COOR', —$CH_2OR''$ and —OR" groups being of either configuration with respect to the pyranose rings;
(iii) Minoxidil and its derivatives,
(iv) Minoxidil glucuronides,
(v) Minoxidil sulphates,
(vi) Direct proteoglycanase inhibitors, such as 1,10-phenanthroline.
(vii) Glycosaminoglycanase inhibitors, such as aldonolactones and esterified aldonolactones having the structure (53):

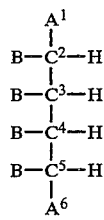

(53)

where $A^1$ and $A^6$ are

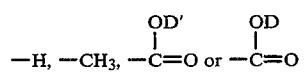

B is OD" or a lactone linkage to position 1 or 6, or —NHCOCH$_3$
and where D is —H or C$_2$ to C$_8$ alkyl, D' is the remainder of the molecule joined through another C atom at positions 2 to 5 to form a lactone, D" is —H or C$_2$ (i.e. acetyl) to C$_4$ acyl of either configuration with respect to the backbone of this molecule;

preferred examples of which include:
L-Galactono-1,4-lactone
L-Arabino-1,5-lactone
D-Fucono-1,5-lactone
D-Glucaro-1,4-lactone
D-Glucurono-6,3-lactone
Galactaric acid lactone
2-Acetamido-2-deoxygluconolactone
2-Acetamido-2-deoxygalactono-lactone
D-Glucaro-1,4:6,3-dilactone
L-Idaro-1,4-lactone
2,3,5-Tri-0-acetyl-D-glucaro-1,4-lactone
2,5-Di-0-acetyl-D-glucaro-1,4:6,3-dilactone (viii) Glycosaminoglycanase inhibitors, such as monosaccharides and esterified monosaccharides having the structure (54):

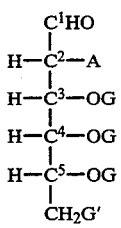
(54)

where
A is —OR or —NHCOCH$_3$
G is —H, —SO$_3$M", C$_2$ (i.e. acetyl) to C$_4$ acyl
G' is —H or —OR
M" is —H or a metal cation wherein the functional groups can be in either configuration with respect to the backbone of the above molecule;

preferred examples of which include:
N-Acetylglucosamine
N-Acetylgalactosamine
D-Galactosamine
D-Glucosamine-3-sulphate
N-Acetylmannosamine (ix) glycosaminoglycan chain cellular uptake inhibitors such as, hexuronic acid and esters thereof which may be represented by the generic structure (55):

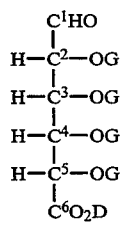
(55)

where
G is —H, —SO$_3$M", C$_2$ (i.e. acetyl) to C$_4$ acyl;
D is —H or C$_2$ to C$_8$ alkyl
M" is —H or a metal cation;

wherein the functional groups can be in either configuration with respect to the backbone of the above molecule;

(x) Chemical inhibitors of glycosidase activity chosen from lactams having the structure (56):

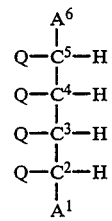
(56)

where A$^1$ and A$^6$ are

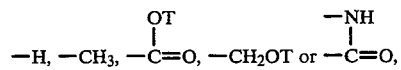

A$^1$ and A$^6$ being the same or different, and at least one of which being the group:

in a lactam ring;

and where Q is —OT', —NHT' or a lactam linkage to A$^1$ to A$^6$;

the Q groups being the same or different, and at least one of which is involved in a lactam linkage;

and where T is the same or different and is chosen from —H, —C$_p$H$_{2p+1}$ or a metal ion, T' is —H or —COC$_p$H$_{2p+1}$, and p is an integer of from 1 to 22;

provided that:

where any of the Q groups is —OT' or —NHT',
then that group or groups can be of either stereochemical configuration with respect to the plane of the ring, preferred examples of which include:
D-glucaro-1,5-lactam
L-Galactono-1,4-lactam,
L-Arabino-1,5-lactam,
D-Fucono-1,5-lactam,
D-Glucaro-1,4-lactam,
D-Glucurono-6,3-lactam,
1,2,5-tri-O-acetyl-D-glucurono-6,3-lactam
2-Acetamido-2-deoxygluconolactam,
2-Acetamido-2-deoxygalactonolactam,
D-Glucaro-1,4:6,3-dilacteun,
L-Idaro-1,4-lactam,
2,3,5-Tri-O-acetyl-D-glucaro-4-lactam,
2,5-Di-O-acetyl-D-Glucaro-1,4:6,3-dilactam,
D-glucaro-1,5-lactam ethyl ester;

(b) Penetration Enhancers

As has been stated earlier, the presence of a penetration enhancer can potentiate the benefit of the chemical activator by improving its delivery through the stratum corneum to its site of action in the immediate environment of the hair follicle close to the dermal papilla.

The penetration enhancer can accordingly function in a variety of ways. It can for example, improve the distribution of the chemical activator on the skin surface or, it can increase its partition into the skin from the composition when applied topically, so aiding its passage to its site of action. Other mechanisms enhancing the benefit of the chemical activator may also be involved.

Examples of penetration enhancers include:
2-methyl propan-2-ol
Propan-2-ol
Ethyl-2-hydroxypropanoate
Hexan-2,5-diol
POE(2) ethyl ether
Di(2-hydroxypropyl) ether
Pentan-2,4-diol
Acetone
POE(2) methyl ether
2-hydroxypropionic acid
2-hydroxyoctanoic acid
Propan-1-ol
1,4 Dioxane
Tetrahydrofuran
Butan-1,4-diol
Propylene glycol dipelargonate
Polyoxypropylene 15 stearyl ether
Octyl alcohol
POE ester of oleyl alcohol
Oleyl alcohol
Lauryl alcohol
Dioctyl adipate
Dicapryl adipate
Diisopropyl adipate
Diisopropyl sebacate
Dibutyl sebacate
Diethyl sebacate
Dimethyl sebacate
Dioctyl sebacate
Dibutyl suberate
Dioctyl azelate
Dibenzyl sebacate
Dibutyl phthalate
Dibutyl azelate
Ethyl myristate
Dimethyl azelate
Butyl myristate
Dibutyl succinate
Didecyl phthalate
Decyl oleate
Ethyl caproate
Ethyl salicylate
Isopropyl palmitate
Ethyl laurate
2-ethyl-hexyl pelargonate
Isopropyl isostearate
Butyl laurate
Benzyl benzoate
Butyl benzoate
Hexyl laurate
Ethyl caprate
Ethyl caprylate
Butyl stearate
Benzyl salicylate
2-hydroxypropanoic acid
2-hyroxyoctanoic acid, Yet further penetration enhancers include esters of pyroglutamic acid having the structure (58):

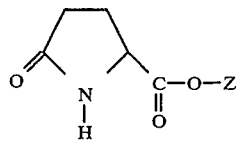
(58)

where
Z is $C_1$ to $C_{30}$ alkyl, or

and where Z' and Z" are the same or different and are each represented by H or the grouping (59): [$(CH_3)_u$, $(CH_2OH)_v$, $(CH_2)_w$, $(CH_3CH_2)_s$, $(CH=CH)_z$]- (59)
where u is zero or 1
v is zero, or the integer 1 or 2,
w is zero, or an integer of from 1 to 21
s is zero, or an integer of from 1 to 4,
y is zero, or the integer 1 or 2,
z is zero, or an integer of from 1 to 22, and
u+v+w+x+y+z is an integer of from 1 to 22;
provided that when the subgrouping (CH=CH) is present, then the total number of carbon atoms in said grouping is from 10 to 22.

Examples of suitable esters of pyroglutamic acid where Z in structure (53) is $C_1$ to $C_{30}$ alkyl are:
pyroglutamic acid methyl ester
pyroglutamic acid ethyl ester
pyroglutamic acid n-propyl ester
pyroglutamic acid n-butyl ester
pyroglutamic acid n-heptyl ester
pyroglutamic acid n-octal ester
pvroglutamic acid n-nonyl ester
pyroglutamic acid n-decyl ester
pyroglutamic acid n-undecyl ester
pyroglutamic acid n-dodecyl ester
pyroglutamic acid n-tridecyl ester
pyroglutamic acid n-tetradcyl ester
pyroglutamic acid n-hexadecyl ester
pyroglutamic acid n-octadecyl ester
pyroglutamic acid n-eicosyl ester
pyroglutamic acid iso-propyl ester
pyroglutamic acid 2-methylhexyl ester
pyroglutamic acid 2-ethylhexyl ester
pyroglutamic acid 3,7-dimethyloctyl ester
pyroglutamic acid 2-hexyldecyl ester
pyroglutamic acid 2-octyldodecyl ester
pyroglutamic acid 2,4,4-trimetyl-1-pentane ester
pyroglutamic acid methyloctyl ester Particularly preferred esters of this group are those where Z in structure (1) is $C_1$ to $C_{14}$ alkyl, (linear or branched), especially $C_1$ to $C_6$ (linear or branched).

Further examples of preferred esters of pyroglutamic acid, where Z in structure (58) is

are those where Z' and/or Z" having the structure shown for grouping (59), include straight and branched chain, saturated or unsaturated aliphatic groups having from 1 to 22 carbon atoms, such as the alkyl groups:
methyl ethyl
propyl
iso-propyl
butyl
iso-butyl
n-valeryl
iso-valeryl
n-caproyl
n-heptyl
n-caprylyl
n-capryl
lauryl
myristyl
palmityl
stearyl, and
arachidyl.
and the $C_{10-22}$ alkenyl groups:
linoleyl
linolenyl
δ-linolenyl
arachidonyl, and
columbinyl.

Further examples of the grouping (59) also include hydroxyalkyl groups having from 1 to 22 carbon atoms, such as:
hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-buty
12-hydroxystearyl.

It is to be understood that the above list is not exhaustive, there being many other examples of alkyl or substituted alkyl groups expressed by the above generic grouping (59).

Further specific examples of esters of pyroglutamic acid which are particularly suited to use as penetration enhancers are:
2-[pyroglutamoyloxy]-propionic acid
methyl -2-[pyroglutamoyloxy]-acetate
ethyl- 2-[pyroglutamoyloxy]-n-propionate
ethyl- 2-[pyroglutamoyloxy]-n-butyrate
ethyl- 2-[pyroglutamoyloxy]-iso-butyrate
ethyl- 2-[pyroglutamoyloxy]-n-valerate
ethyl- 2-[pyroglutamoyloxy]-n-caproate
ethyl- 2-[pyroglutamoyloxy]-n-heptylate
ethyl- 2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

It is to be understood that the above lists of specific examples of esters of pyroglutamic acid are not exhaustive, there being many other examples expressed by the generic structure of these esters.

Further examples of penetration enhancers include:
Dimethyl sulphoxide
N,N-Dimethyl acetamide
N,N-Dimethyl formamide
2-Pyrrolidone
1-Methyl-2-pyrrolidone
5-Methyl-2-pyrrolidone
1,5-Dimethyl-2-pyrrolidone
1-Ethyl-2-pyrrolidone
Phosphine oxides
Sugar esters
Tetrahydrofurfural alcohol
Urea
Diethyl-m-toluamide, and
1-Dodecylazacyloheptan-2-one Further examples of penetration enhancers include surface active agents, preferred examples of which include:
(i) Anionic surface active agents, such as metallic or alkanolamine salts of fatty acids for example sodium laurate and triethanolamine oleate;
alkyl benzene sulphonates, for example triethanolamine dodecyl benzene sulphonate;
alkyl sulphates, for example sodium lauryl sulphate;
alkyl ether sulphates, for example sodium lauryl ether sulphate [2 to 8 EO];
sulphosuccinates, for example sodium dioctyl sulphonsuccinate;
monoglyceride sulphates, for example sodium glyceryl monostearate monosulphate;
isethionates, for example sodium isethionate;
methyl taurides, for example Igepon T;
acylsarcosinates, for example sodium myristyl sarcosinate;
acyl peptides, for example Maypons and Lamepons;
acyl lactylates,
polyalkoxylated ether glycollares, for example trideceth-7 carboxylic acid;
phosphates, for example sodium dilauryl phosphate.
(ii) Cationic surface active agents, such as a/nine salts, for example sapamin hydrochloride;
quarternary ammonium salts, for example Quaternium 5, Quaternium 31 and Quaternium 18;
(iii) Amphoteric suface active agents, such as imidazol compounds, for example Miranol;
N-alkyl amino acids, such as sodium cocaminopropionate and asparagine derivatives;
betaines, for example cocoamidopropylbetaine
(iv) Nonionic surface active agents, such as fatty acid alkanolamides, for example oleic ethanolamide;
esters of polyalcohols, for example Span;
polyglycerol esters, for example that esterified with $C_{12-18}$ fatty acids and one or several OH groups;
polyalkoxylated derivatives, for example polyoxy:-polyoxyethylene stearate, and octylphenoxy polyethoxyethanol (TRITON X-100);
ethers, for example polyoxyethylene lauryl ether;
ester ethers, for example Tween;
amine oxides, for example coconut and dodecyl dimethyl amine oxides.

Mixtures of two or more of the above surface active agents can be employed in the composition according to the invention.

(c) cationic polymers chosen from:

Guar Hydroxypropyltrimonium chloride
Quaternium-19
Quaternium-23
Quaternium-40
Quaternium-57
Poly(dipropyldiallylammonium chloride)
Poly(methyl-δ-propaniodiallylammonium chloride)
Poly(diallylpiperidinium chloride)
Poly(vinyl pyridinium chloride)
Quaternised poly (vinyl alcohol)
Quaternised poly (dimethylaminoethylmethacrylate); and mixtures thereof.

The amount of vehicle in the composition, including water if present, should be sufficient to carry at least a portion of the chemical activator to the skin in an amount which is sufficient effectively to enhance skin quality and/or hair growth. The amount of the vehicle can comprise the balance of the composition, particularly where little or no other ingredients are present in the composition. Accordingly, the vehicle or vehicles can comprise from 0.1 to 99.999999%, preferably from 50 to 99% by weight of the composition.

When the vehicle is an activity enhancer, the amount present when employed in accordance with the invention, will normally be from 0.1 to 50%, preferably from 0.5 to 25% and most preferably from 0.5 to 10% by weight of the composition.

(d) Iontophoresis

A further means for enhancing the activity of the chemical activator following topical application is the use of iontophoresis. A preferred iontophoretic device for this purpose comprises a pad of absorbent material, such as a nonwoven sheet or sponge, impregnated with a solution of the chemical activator as herein defined, the pad carrying an electrode, for example in the form of a metallic sheet, through which an electric current can be passed, in order to enhance delivery of the chemical activator to and through the epidermal layer of the skin.

Further preferred embodiments of the invention

Further preferred embodiments of the invention are those where the composition according to the invention comprises a second hair growth stimulant in addition to at least one chemical activator, as herein defined.

Particularly preferred mixtures include the following, where minoxidil can be employed in compositions according to the invention with a diacylglycerol.

Accordingly, preferred mixtures are:
Minoxidil and 1,2-dipentadecanoyl-sn-glycerol
Minoxidil and 1,2-diseptadecanoyl-rac-glycerol
Minoxidil and 1-Oleoyl-2-acetyl-rac-glycerol
Minoxidil and 1-Stearoyl-2-arachidonoyl-syn-glycerol
Minoxidil and 1,2-dioleoyl-sn-glycerol
Minoxidil and 1-oleoyl-2-acetyl-sn-glycerol Perfume The composition according to the invention can also optionally comprise a perfume in an amount sufficient to make the composition acceptable to the consumer and pleasant to use. Usually, the perfume will form from 0.01 to 10% by weight of the composition.

Other hair growth promoter adjuncts

The composition according to the invention can also contain adjuncts other than those already mentioned, depending on the form of the intended product. It is, for example, possible to include antiseptics, preservatives, antioxidants, emulsifiers and colouring agents, which can improve the stability and consumer appeal of the composition.

The composition according to the invention can also be employed as a vehicle for a wide variety of cosmetically or pharmaceutically active ingredients, including ingredients which have some beneficial effect other than the promotion of hair growth when applied to the skin. An example of such pharmaceutically active ingredients are anti inflammatory agents, such as steroidal (e.g., corticosteroids, especially hydrocortisone) and non-steroidal (e.g., ibuprofen and its derivatives) compounds.

PROCESS

The invention also provides a process for the preparation of a composition for administration to mammalian skin or hair, which process comprises the step of mixing a chemical activator, as herein defined, with a suitable vehicle to provide a composition according to the invention, in which the activator forms from 0.000001 to 99.9% by weight of the composition.

Product Form

The composition of the invention can be formulated as a liquid, for example as a lotion, shampoo, conditioner or milk for use in conjunction with an applicator such as a roll-ball applicator, or a spray device such as an aerosol can containing propellant, or a container fitted with a pump to dispense the liquid product.

When the composition is contained in a pressurised aerosol container, the propellant in providing an inert headspace within the container will aid in preserving the composition.

The composition of the invention can also be solid or semi-solid, for example a stick, cream or gel, for use in conjunction with a suitable applicator or simply a tube, bottle or lidded jar, or as a liquid-impregnated fabric, such as a tissue wipe.

The invention accordingly also provides a closed container containing a composition as herein defined. cl Use of the Chemical Activator for Inducing, Maintaining or Increasing Hair Growth The invention also provides for the use of a chemical activator as herein defined, for topical application to mammalian hair or skin particularly the scalp, for inducing, maintaining or increasing terminal hair growth, and/or converting vellus hair to growth as terminal hair.

The composition of the invention is accordingly primarily intended for topical application to the scalp of the human subject, particularly where the head is already bald or balding, in order to reduce or prevent the onset of baldness.

The invention also provides for the use of the chemical activator in the preparation of a therapeutic composition for treating baldness.

The amount of the composition and the frequency of application to the hair and/or scalp can vary widely, depending on personal needs, but it is suggested as an example that topical application of from 0.1 to 5 g daily containing from 0.00001 to 1 g of a selected chemical activator over the period of at least six months will in most cases result in an improvement in hair growth.

EVALUATION OF EFFICACY OF CHEMICAL ACTIVATORS USING THE RAT MODEL

The Rat Hair Growth Test

The effect of compounds on hair growth was assessed using male albino Wistar rats as an animal model. The rats were chosen from as few litters as possible and were each approximately 42 days of age at the start of the test. Each rat was housed individually to prevent licking.

In each comparison, 10 rats were used in each group and hair growth was assessed as follows:

A small patch of normal skin (4cm ×4cm) on the upper back of each rat was clipped at the start and 0.3 ml of a hair growth stimulant composition (or a control) applied topically twice daily and once on Saturdays and Sundays to each clipped area. The concentration of test compound in the composition was 0.2 mg/ml.

Hair was clipped from the area of the patch twice weekly, collected and weighed at each time point over a standard period of 3 months, and cumulative hair weight calculated. From these data, it was possible to estimate the effect of a hair growth stimulant as a test compound on the amount and duration of hair growth during the experiment. A positive response, i.e. an increase of at least 10% by weight of hair after 3 months treatment, compared with a control indicates the potential of the test compound to prevent hair loss and/or reverse baldness in human subjects.

Accordingly, when the chemical activators, as herein defined, are assessed either individually or in combination as test compounds by the Rat Hair Growth Test, an increase of at least 10% by weight of hair after 3 months treatment will be obtained. Usually, the 10% by weight minimum value will be attained well before the end of this 3 month period.

(ii) Validation of rat model for hair growth using Minoxidil

The rat model was validated by showing that twice daily topical application of a known promoter of human hair growth, namely 2% (w/v) minoxidil in a vehicle of 70% ethanol, 20% water and 10% propylene glycol, caused a significant increase of 25% in hair growth as shown below:

TABLE 1

| Treatment | Mean Cumulative Hair weight (mg) ± sd, after 52 days | Significance Level (vs vehicle) |
|---|---|---|
| 2% minoxidil | 786.2 ± 94.8 | p = 0.002* |
| Vehicle (control) | 628.3 ± 90.0 | |

*statistically significant (iii) Measurement of hair growth following topical application of 1-oleoyl-2-acetyl-sn-glycerol as chemical activator and acetone as activity enhancer Topical treatment with a composition according to the invention was found to stimulate hair growth. In this example, the effect of topical application of 1-oleoyl-2-acetyl-sn-glycerol, and activator of protein kinase C, is shown. The test solution in this experiment contained 40% (w/v) of the diacylglycerol in the form of a solution in acetone. The acetone functioned both as vehicle and preservative. Test or control solutions (0.1 ml) were applied once per week to the clipped site; the hair growth results are shown in Table 2.

TABLE 2

| Treatment | Mean Cumulative Hair Weight (mg) ± sd, after 38 days | Significance Level (vs vehicle) |
|---|---|---|
| % Diacylglycerol | 381.1 ± 85.0 | p < 0.006* |
| Vehicle (control) | 289.4 ± 40.2 | |

*statistically significant

In addition to demonstrating a statistically significant stimulation of hair growth (a 32% increase) as shown in Table 2, the diacylglycerol has been consistently found to advance anagen, thus reducing the amount of time spent in the resting stage of hair cycle.

EXAMPLES

The invention is illustrated by the following examples:

Example 1

This Example illustrates a lotion according to the invention which is suitable for topical application to the scalp in order to promote hair growth.

The lotion has the following formulation:

| | % w/w |
|---|---|
| 1,2-dihexanoyl-sn-glycerol | 1 |
| ethanol | 99 |
| perfume | q.s. |

Example 2

This Example illustrates a hair tonic which is suitable for application to hair or scalp.

The hair tonic has the following formulation:

| | % w/w |
|---|---|
| 1,2-dioctanoyl-rac-glycerol | 2 |
| ethanol | 50 |
| sorbic acid | 1 |
| water | 47 |
| perfume | q.s. |

Example 3

This Example also illustrates a lotion which is suitable for topical application to the scalp.

The lotion has the following formulation:

| | % w/w |
|---|---|
| 1-Oleoyl-2-acetyl-rac-glycerol | 20 |
| propanol-2-ol | 10 |
| ethanol | 68 |
| sodium benzoate | 2 |
| perfume | q.s. |

EXAMPLE 4

This Example also illustrates a hair tonic which is suitable for application to hair or scalp.

The hair tonic has the following formulation:

|  | % w/w |
|---|---|
| 1,2-dioleoyl-syn-glycerol | 15 |
| ethanol | 40 |
| methyl p-hydroxybenzoic acid | 1 |
| water | 44 |
| perfume | q.s. |

Examples 5 to 8

The following formulations represent lotions which can be used topically in the treatment of bald or balding male or female heads.

| | % w/w | | | |
|---|---|---|---|---|
| | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| 1,2-dioleoyl-sn-glycerol | 5 | — | — | — |
| 1-oleoyl-2-acetyl-sn-glycerol | — | 1 | — | — |
| 1,2-dihexanoyl-sn-glycerol | — | — | 0.8 | — |
| Minoxidil | 1 | 1 | 1 | 1 |
| Perfume | 1 | 1 | 1 | 1 |
| Benzoic acid | 1 | 1 | 1 | 1 |
| Water to | 100 | 100 | 100 | 100 |

I claim:

1. A preserved composition suitable for topical application to mammalian skin or hair which comprises:
   (i) a chemical activator of protein kinass C enzymes chosen from diacylglycerols having the structure (1):

where X is the same or different, is limited to X having a chain length containing at least 15 carbon atoms and is represented by the grouping:

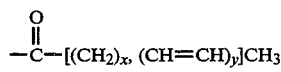

where
x' is an integer of from 13 to 28, and y is 0, or an integer of from 1 to 5:
the OX groups being of either stereochemical configuration with respect to one another and to the carbon backbone of the glycerol molecule, and the double bonds being of either cis or trans configuration; and
   (ii) a cosmetically acceptable vehicle for the chemical activator present in an amount from 0.00001 to 99.9% by weight of the composition.

2. The composition of claim 1, wherein the diacylglycerol is selected from the group consisting of:
1-Stearoyl-2-arachidonoyl-sn-glycerol
1,2- Distearoyl-rac-glycerol
1,2-Dipentadecanoyl-sn-glycerol
1,2-Dipentadecanoyl-rac-glycerol
1,2-Dipalmitoyl-rac-glycerol
1,2-Dipalmitoyl-sn-glycerol
1,2-Diseptadecanoyl-rac-glycerol
1,2-Dioleoyl-sn-glycerol
1,2-Dioleoyl-rac-glycerol
1,2-Diarachidonoyl-sn-glycerol
1,2-Dieicosanoyl-sn-glycerol
1,2-Didoeicosanoyl-rac-glycerol, and
1,2-Dioctaeicosanoyl-sn-glycerol.

3. The composition of claim 1, further comprising a penetration enhancer present in an effective amount to enhance activity of said chemical activator, said penetration enhancer being selected from a group consisting of:
1-dodecylazacycloheptan-2-one
dibutyl sebacate
2-hydroxyoctanoic acid
esters of pyroglutamic acid and mixtures thereof.

4. The composition of claim 1, further comprising a cationic polymer present in an effective amount to enhance activity of said chemical activator, said cationic polymer being selected from the group consisting of:
Guar Hydroxypropyltrimonium chloride
Quaternium-19
Quaternium-23
Quaternium-40
Quaternium-57
Poly (dipropyldiallylammonium chloride)
Poly (methyl-δ-propaniodiallylammonium chloride)
Poly(diallylpiperidinium chloride)
Poly(vinyl pyridinium chloride)
Quaternised poly (vinyl alcohol)
Quaternised poly (dimethylaminoethylmethacrylate); and mixtures thereof.

5. A method for convening vellus hair to growth as terminal hair which comprises the step of applying to the scalp in the region of vellus hair an effective amount of a preserved composition comprising;
   (i) a chemical activator of protein kinase C enzymes chosen from diacylalycerols having the structure (1):

where X is the same or different, is limited to X having a chain length containing at least 15 carbon atoms and is represented by the grouping:

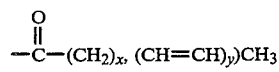

where
x' is an integer of from 13 to 28, and y is O or an integer of from 1 to 5:
the OX groups being of either stereochemical configuration with respect to one another and to the carbon backbone of the glycerol molecule, and the double bonds being of either cis or trans configuration: and
   (ii) a cosmetically acceptable vehicle for the chemical activator present in an amount from 0.00001 to 99.9% by weight of the composition.

6. A method for increasing the rate of terminal hair growth, which comprises the step of applying to the scalp in the region of terminal hair an effective amount of a preserved composition comprising:

(i) a chemical activator of protein kinass C enzymes chosen from diacylglycerols having the structure (1):

$$\begin{array}{l} H_2-C-OH \\ H-C-OX \\ H_2-C-OX \end{array} \quad (1)$$

where X is the same or different is limited to X having a chain length containing at least 15 carbon atoms and is represented by the grouping:

$$-\overset{O}{\underset{\|}{C}}-[(CH_2)_{x'}(CH=CH)_y]CH_3$$

where
x' is an integer of from 13 to 28, and y is O, or an integer of from 1 to 5;
the OX groups being of either stereochemical configuration with respect to one another and to the carbon backbone of the glycerol molecule, and the double bonds being of either cis or trans configuration; and (ii) a cosmetically acceptable vehicle for the chemical activator present in an amount from 0.00001 to 99.9% by weight of the composition.

7. The composition of claim 1, wherein the diacylglycerol is dioleoylglycerol.

8. A preserved cosmetic composition suitable for topical application to mammalian skin or hair which comprises:

(i) from 0.000001 to 99.9% by weight of the composition of a chemical activator of protein kinase C enzymes chosen from diacylglycerols having the structure:

$$\begin{array}{l} H_2-C-OH \\ H-C-OX \\ H_2-C-OX \end{array} \quad (1)$$

where X is the same or different, and is represented by the grouping:

$$-\overset{O}{\underset{\|}{C}}-[(CH_2)_{x'}(CH=CH)_y]CH_3$$

where
x' is an integer of from 13 to 28, and y is O or an integer of from 1 to 5;
the OX groups being of either stereochemical configuration with respect to the carbon backbone of the glycerol molecule, and the double bonds being of either cis or trans configuration; and (ii) a cosmetically acceptable vehicle for the chemical activator present in an effective amount to deliver the chemical activator to the mammalian skin or hair; the composition being preserved so as to be free from microbial contaminants capable of resulting in microbial spoilage of the composition and/or biodegradation of the chemical activator.

* * * * *